(12) United States Patent
Gao et al.

(10) Patent No.: US 10,507,278 B2
(45) Date of Patent: Dec. 17, 2019

(54) FLUIDIC DEVICES, METHODS, AND SYSTEMS

(71) Applicant: Boston Scientific Scimed, Inc., Maple Grove, MN (US)

(72) Inventors: Wei Alfred Gao, Shanghai (CN); Cheng Zhang, Vadnais Heights, MN (US); Yuan Chester Hong, Shanghai (CN); Feng Kevin Xu, Shanghai (CN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 409 days.

(21) Appl. No.: 15/233,743

(22) Filed: Aug. 10, 2016

(65) Prior Publication Data
US 2017/0333614 A1 Nov. 23, 2017

(30) Foreign Application Priority Data
May 23, 2016 (CN) .......................... 2016 1 0344880

(51) Int. Cl.
*A61M 1/34* (2006.01)
*A61B 18/26* (2006.01)
(Continued)

(52) U.S. Cl.
CPC ........... *A61M 1/3403* (2014.02); *A61B 17/22* (2013.01); *A61B 17/22012* (2013.01);
(Continued)

(58) Field of Classification Search
CPC .............. A61M 1/0025; A61M 1/0056; A61M 1/3403; A61M 39/22; A61B 18/26; A61B 17/22

See application file for complete search history.

(56) References Cited

U.S. PATENT DOCUMENTS

| 4,423,727 A | 1/1984 | Widran et al. |
| 5,702,607 A * | 12/1997 | Lawson ................. B01D 29/27 134/111 |

(Continued)

OTHER PUBLICATIONS

International Search Report and Written Opinion issued in International Application No. PCT/US2017/033847, dated Sep. 7, 2017 (12 pages).

*Primary Examiner* — Phong Son H Dang
(74) *Attorney, Agent, or Firm* — Bookoff McAndrews, PLLC

(57) ABSTRACT

Fluidic devices, methods, and systems are disclosed. One system may comprises a sheath, a delivery module, and a removal module. The sheath includes a working lumen, a delivery lumen, and a removal lumen. The delivery module is configured to move a fluid from a fluid reservoir and into a body cavity through the delivery lumen. The removal module is configured to move the fluid and a particulate contained therein out of the body cavity through the removal lumen, through a filtration device that removes the particulate, and back into the fluid reservoir. One method comprises placing a distal end of sheath into a body cavity, energizing the working lumen to generate a particulate in the cavity, moving the fluid into the cavity to engage the particulate, and moving the fluid and the contaminant from the body cavity, through a filter for removing the contaminant, and back into the fluid source.

17 Claims, 5 Drawing Sheets

(51) Int. Cl.
  *A61M 39/22* (2006.01)
  *A61M 1/00* (2006.01)
  *A61B 17/22* (2006.01)
  *A61B 18/20* (2006.01)
  *A61B 18/00* (2006.01)

(52) U.S. Cl.
  CPC ............ *A61B 18/26* (2013.01); *A61M 1/0025* (2014.02); *A61M 1/0056* (2013.01); *A61M 1/0058* (2013.01); *A61M 39/22* (2013.01); *A61B 2017/22072* (2013.01); *A61B 2017/22079* (2013.01); *A61B 2017/22084* (2013.01); *A61B 2018/00791* (2013.01); *A61B 2018/00898* (2013.01); *A61B 2018/00982* (2013.01); *A61B 2018/206* (2013.01); *A61B 2217/005* (2013.01); *A61B 2217/007* (2013.01); *A61B 2218/002* (2013.01); *A61M 2205/3344* (2013.01); *A61M 2205/3368* (2013.01); *A61M 2230/005* (2013.01); *A61M 2230/30* (2013.01)

(56) References Cited

U.S. PATENT DOCUMENTS

| | | |
|---|---|---|
| 5,817,144 A | 10/1998 | Gregory |
| 5,944,687 A * | 8/1999 | Benett .................... A61B 18/26 604/22 |
| 6,159,160 A * | 12/2000 | Hsei .................... A61M 1/0058 600/560 |
| 6,179,824 B1 * | 1/2001 | Eggers .................... A61B 18/12 604/28 |
| 6,203,537 B1 * | 3/2001 | Adrian .................... A61B 18/26 601/4 |
| 6,375,651 B2 | 4/2002 | Grasso, III et al. |
| 6,379,325 B1 * | 4/2002 | Benett .................... A61B 18/26 604/22 |
| 6,409,677 B1 * | 6/2002 | Tulkki .................... A61B 5/01 600/549 |
| 6,733,664 B2 | 5/2004 | Menne et al. |
| 7,505,812 B1 * | 3/2009 | Eggers .................... A61B 18/12 604/20 |
| 8,192,424 B2 * | 6/2012 | Woloszko .......... A61B 18/1206 606/40 |
| 8,512,326 B2 * | 8/2013 | Shadduck .............. A61B 18/18 606/32 |
| 8,568,424 B2 * | 10/2013 | Shugrue ........... A61B 17/32002 606/119 |
| 8,728,066 B2 * | 5/2014 | Shadduck .............. A61B 18/18 606/32 |
| 9,125,550 B2 * | 9/2015 | Shener-Irmakoglu ........................ A61B 1/00068 |
| 9,233,193 B2 * | 1/2016 | Truckai ............... A61M 1/0031 |
| 9,498,244 B2 * | 11/2016 | Orczy-Timko ................................ A61B 17/32002 |
| 9,597,149 B2 * | 3/2017 | Germain ................ A61B 50/13 |
| 9,901,665 B2 * | 2/2018 | Klein .................. A61M 1/0064 |
| 9,907,563 B2 * | 3/2018 | Germain ................ A61B 17/22 |
| 2002/0002366 A1 * | 1/2002 | Grasso, III ............ A61B 18/26 606/2.5 |
| 2005/0245894 A1 * | 11/2005 | Zadno-Azizi .... A61B 17/12045 604/509 |
| 2006/0047185 A1 * | 3/2006 | Shener .............. A61B 1/00068 600/156 |
| 2007/0021713 A1 * | 1/2007 | Kumar .................. A61M 1/006 604/27 |
| 2007/0106175 A1 * | 5/2007 | Uchiyama .............. A61B 1/041 600/564 |
| 2007/0249993 A1 * | 10/2007 | Mollstam ............... A61B 1/015 604/65 |
| 2008/0004621 A1 * | 1/2008 | Dahla .................. A61B 18/148 606/48 |
| 2008/0091061 A1 * | 4/2008 | Kumar ............... A61B 1/00068 600/104 |
| 2008/0091071 A1 * | 4/2008 | Kumar ............... A61B 1/00068 600/121 |
| 2008/0243054 A1 * | 10/2008 | Mollstam ............... A61B 1/015 604/31 |
| 2008/0275383 A1 * | 11/2008 | Weisel .................... A61B 17/22 604/35 |
| 2009/0163846 A1 | 6/2009 | Aklog et al. |
| 2009/0270896 A1 * | 10/2009 | Sullivan ........... A61B 17/32002 606/170 |
| 2009/0270898 A1 * | 10/2009 | Chin ....................... A61B 1/303 606/170 |
| 2010/0137847 A1 * | 6/2010 | Cecchetti ............... A61B 18/26 606/2.5 |
| 2012/0172888 A1 * | 7/2012 | Shugrue .......... A61B 17/32002 606/119 |
| 2013/0131445 A1 * | 5/2013 | Zerfas ................... A61B 17/22 600/104 |
| 2013/0296847 A1 * | 11/2013 | Germain .............. A61B 18/1206 606/39 |
| 2013/0331758 A1 * | 12/2013 | Meibaum .............. A61M 1/30 604/5.04 |
| 2014/0303551 A1 * | 10/2014 | Germain ................ A61B 17/22 604/30 |
| 2014/0364765 A1 * | 12/2014 | Callaghan ........... A61M 1/3653 600/581 |
| 2015/0087890 A1 * | 3/2015 | Spanier ................ A61B 5/6852 600/16 |
| 2015/0119795 A1 * | 4/2015 | Germain .............. A61M 3/0229 604/28 |
| 2015/0305759 A1 | 10/2015 | St. George et al. |
| 2016/0206336 A1 * | 7/2016 | Frushour .......... A61B 17/07207 |
| 2016/0262776 A1 * | 9/2016 | Honda .................. A61B 17/22 |
| 2017/0035950 A1 * | 2/2017 | Meyering ............ A61M 1/0098 |
| 2017/0215964 A1 * | 8/2017 | Harrah ................ A61B 1/0125 |
| 2017/0319776 A1 * | 11/2017 | Eisner ................ A61M 3/0283 |
| 2017/0326282 A1 * | 11/2017 | Wilt .................... A61M 1/1086 |
| 2017/0333122 A1 * | 11/2017 | Rajagopalan ......... A61M 29/02 |

\* cited by examiner

FLUIDIC DEVICES, METHODS, AND SYSTEMS

TECHNICAL FIELD

Aspects of the present disclosure generally relate to medical devices and procedures. In particular, some aspects relate to fluidic devices, methods, and systems, such as those used in lithotripsy procedures.

BACKGROUND

Lithotripsy is a medical procedure involving the physical disruption of a hardened mass within a body cavity, such as kidney stones, gallstones, pancreatic stones, or the like. In such procedures, an energy source is typically applied to the hardened mass. Different energy sources can be used, such as electric, hydraulic, laser, mechanical, ultrasound, or the like. Laser lithotripsy is based on the fact that pulsed light energy may be converted into a mechanical energy in the form of a cavitation bubble associated with the occurrence of shock-wave. This mechanical energy is responsible for the disruption of the hardened mass.

A common problem with lithotripsy procedures is that the body cavity is may be polluted by particles disrupted from the hardened mass. For stone-like masses, these particles may be referred to as "stone dust." In laser lithography procedures, this stone dust may hinder visualization of the mass, which prevents the physician from pulsing the laser in the most efficient manner. Fluid may be injected into the body cavity so that a portion of the stone dust will naturally drain out of the body cavity with the fluid. Waiting for the fluid and dust to drain out of the body cavity can be very time consuming, often requiring the physician to prolong the procedure. More fluid may be added to promote drainage, but this may even further prolong the procedure by necessitating the repeated replacement of saline bags.

SUMMARY

Aspects of the present disclosure relate to fluidic devices, methods, and systems. Numerous aspects of the present disclosure are now described.

One aspect of this disclosure is a system that, for example, may comprise a sheath including a working lumen, a delivery lumen, and a removal lumen; a filtration device; a delivery module coupled to a fluid reservoir and the delivery lumen; and a removal module coupled to the removal lumen and the filtration device, wherein the fluid reservoir is coupled to the filtration device so as to define at least one circulation loop when the sheath is placed in a body cavity.

According to this aspect, the at least one sensor may be operable to detect one or more parameters of the fluid or the body cavity. The at least one sensor may be located on a distal end of the sheath. The system may further comprise a controller for operating the delivery and removal modules, for example, in response to the one or more parameters. The at least one sensor may include a pressure sensor, and the one or more parameters of the fluid may include a pressure of the fluid in the body cavity; and/or the at least one sensor may include a blood detector, and the one or more parameters may include an amount of blood in the fluid. The controller may be operable, for example, to prevent the fluid in the body cavity from exceeding a predetermined maximum pressure.

The delivery module may include at least one first pump operable with the controller to move the fluid from the fluid reservoir and into the body cavity through the delivery lumen. The removal module may include at least one second pump operable with the controller to move the fluid and the particulate contained therein out of the body cavity through the removal lumen, through the filtration device, and back into the fluid reservoir. For example, the at least one sensor may include a pressure sensor, the one or more parameters may include a predetermined fluid pressure in the body cavity, and the controller may maintain the predetermined fluid pressure by operation of each of the first and second pumps. The system may further comprise a valve in the circulation loop that is operable with the controller to direct the fluid from the fluid reservoir and back into the filtration device in response to the one or more parameters. Each of the first and second pumps may be removably mounted to a housing of the circulation device. The fluid reservoir and the filtration device, for example, may be removably mounted to the housing.

An exemplary system may further comprise a laser source coupled to the working lumen. Any laser source may be included. The fluid may be saline, and the fluid reservoir may be a saline bag. The filtration device may include one or more filters, any of which may be removably attached thereto. The filtration device may include a sensor operable to detect an amount of blood in the fluid.

Another aspect of this disclosure is a system that, for example, may comprise a sheath including a working lumen, a delivery lumen, and a removal lumen; at least one sensor operable to detect one or more parameters of a fluid or a body cavity; a filtration device; and a circulation device including a first pump coupled to a fluid reservoir and the delivery lumen, a second pump coupled to the removal lumen and the filtration device; and a controller that operates the first and second pumps in response to the one or more parameters, wherein the fluid reservoir is coupled to the filtration device so as to define at least one circulation loop when the sheath is placed in a body cavity.

According to this aspect, the at least one sensor may include one of a pressure sensor, an imaging device, and a temperature sensor. The at least one sensor may be located on the sheath and include a pressure sensor, the one or more parameters may include a predetermined fluid pressure in the body cavity, and the controller may maintain the predetermined fluid pressure by operation of the first and second pumps. This exemplary system may further comprise a valve in the circulation loop that is operable with the controller to direct the fluid from the fluid reservoir and back into the filtration device in response to the one or more parameters. The filtration device may include one or more filters, which may be removably attached thereto. At least the first and second pumps may be removably mounted to a housing of the circulation device. The controller may further comprise an input device and an output device that may be located, for example, on the housing of the circulation device.

Yet another aspect of this disclosure is a method that, for example, may comprise: placing a distal end of sheath into a body cavity, the sheath including a working lumen, a delivery lumen, a removal lumen; energizing the working lumen to generate a particulate in the body cavity; moving, with at least one first pump coupled to the delivery lumen, a fluid from a fluid source into the body cavity to engage the particulate; and moving, with at least one second pump coupled to the removal lumen, the fluid and at least a portion of the contaminant from the body cavity, through at least one filtration device operable to remove the portion of contaminant, and back into the fluid source.

According to this aspect, this exemplary method may further comprise performing a treatment without changing the fluid reservoir, thereby saving operational time and materials. The method may further comprise a controller operably engaged with the first and second pumps, wherein the moving steps may be performed with the controller. The method may further comprise detecting one or more parameters of the fluid or the body cavity with at least one sensor; communicating the one or more parameters of the fluid to the controller; and operating the first and second pumps with the controller in response to the one or more parameters. The at least one sensor may include a pressure sensor, the one or more parameters may include a predetermined fluid pressure in the body cavity, and operating each of the first and second pumps may include maintaining the predetermined fluid pressure in the body cavity. The at least one sensor may include a blood detector, the one or more parameters may include an amount of blood in the fluid, and operating the first and second pumps may include recirculating the fluid through the filtration device to until the amount of blood is reduced.

It may be understood that both the foregoing summary and the following detailed descriptions are exemplary and explanatory only, neither being restrictive of the inventions claimed below.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

The present disclosure is now described with reference to exemplary aspects of fluidic devices, methods, and systems. Some aspects are depicted and/or described with reference to a procedure that generates particulate matter and/or contaminants within a body cavity (together, the "particulate(s)"). A fluid may be circulated through the body cavity to remove the particulates. Any reference to a particular procedure (such as lithotripsy), energy (such as laser energy), force (such suction forces), fluid (such as saline), particulate type (such as stone dust), hardened mass (such as a kidney stone), or body cavity (such as the interior of a kidney) is provided for convenience and not intended to limit the present disclosure unless claimed. Accordingly, the concepts described in this disclosure may be utilized for any analogous device, method, or system—medical or otherwise.

The directional terms "proximal" and "distal" are used to describe relative components and features of the present disclosure. Proximal refers to a position closer to the exterior of the body or a user, whereas distal refers to a position closer to the interior of the body or further away from the user. Unless claimed, these directional terms are provided for convenience and not intended to limit the present disclosure to a particular direction or orientation. As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example," rather than "ideal."

Figure 1:
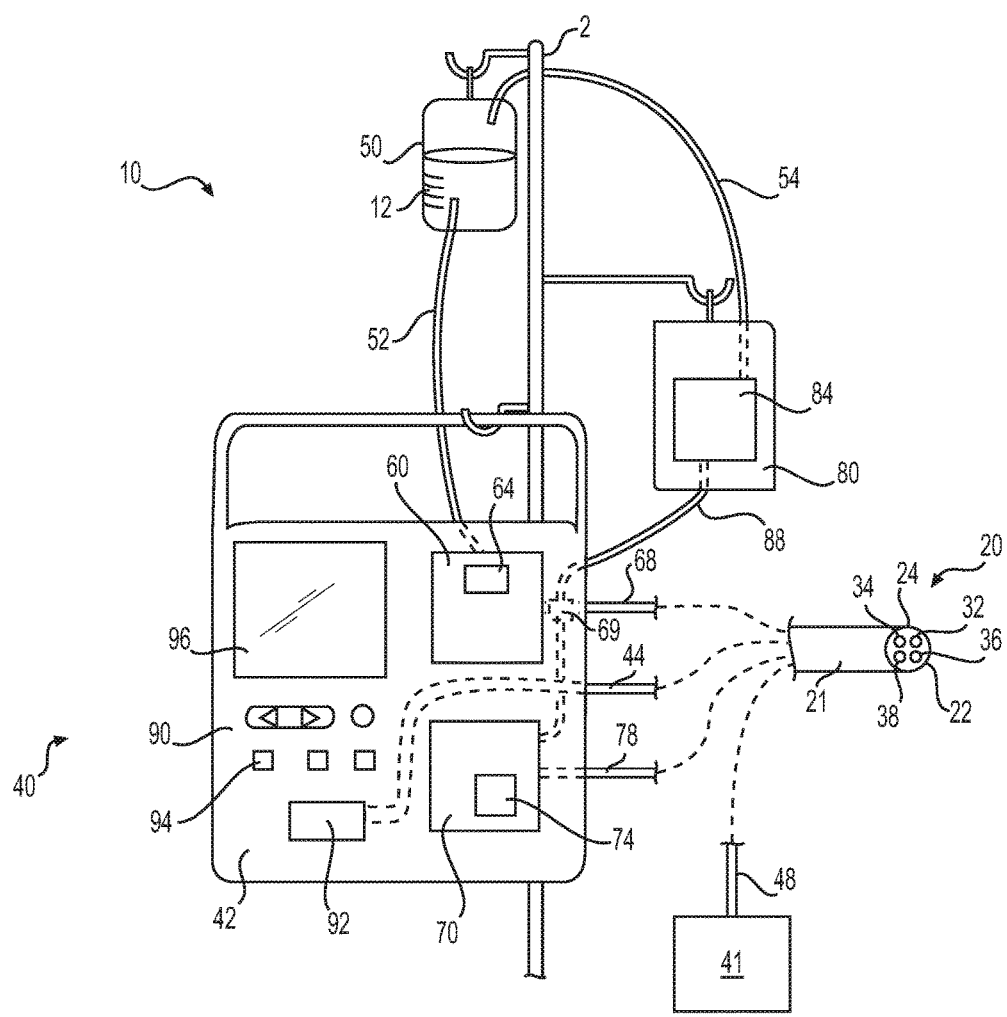
FIG. 1 depicts an exemplary system for removing particulate matter from a body cavity, the system comprising a working device and a circulation device.

An exemplary system 10 is depicted in FIG. 1 as comprising a working device 20 and a circulation device 40. The working and circulation devices 20 and 40 are shown, for example, as being suspended from a rack 2. Aspects of working and circulation devices 20 and 40 are now described.

Figure 2:
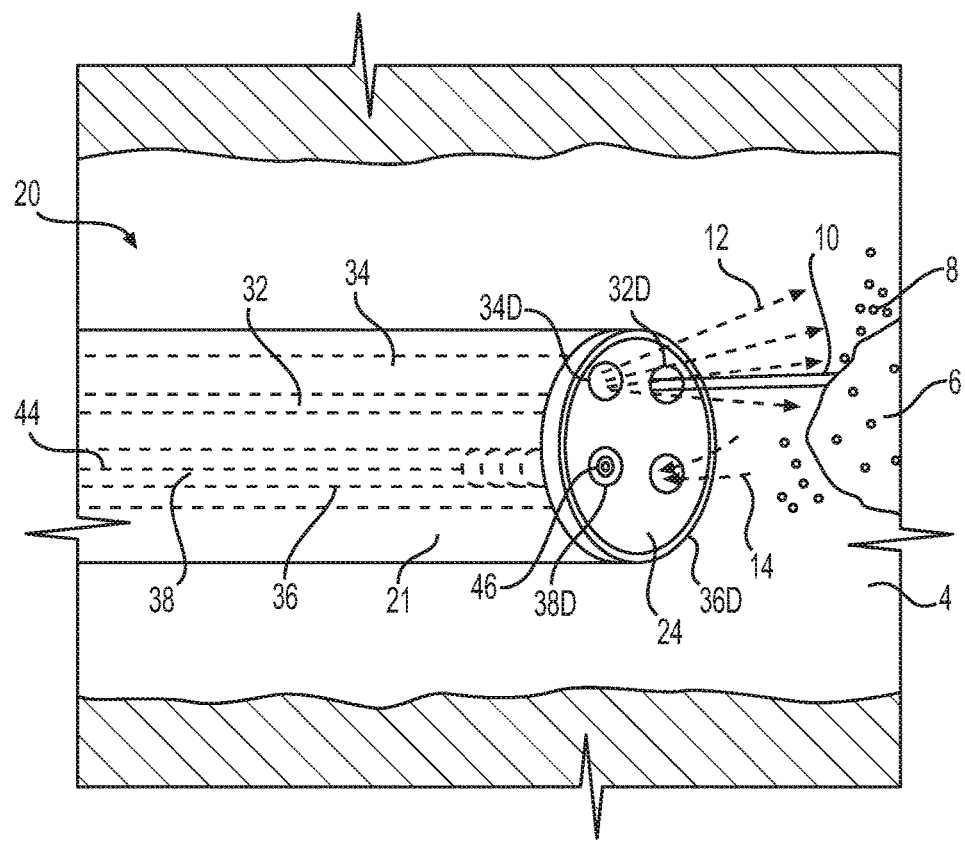
FIG. 2 provides a close-up view of the working device of FIG. 1.

Working device 20 is illustrated in FIGS. 1 and 2, for example, as the distal end 22 of an elongated sheath 21. Device 20 has a working lumen 32, a delivery lumen 34, and a removal lumen 36. As shown in FIG. 2, each lumen has a corresponding distal opening 32D, 34D, or 36D located on a distal face 24 of distal end 22. Lumens 32, 34, and 36 may be used perform a lithotripsy procedure when, for example, distal end 22 is inserted into a body cavity 4, and/or distal face 24 positioned adjacent a hardened mass 6. Each of lumens 32, 34, and 36 may be configured to perform a different function. Working lumen 32, for example, may apply an energy 10 (shown in FIG. 2 as a laser energy) to mass 6, thereby generating particulates 8 in cavity 4. Delivery lumen 34 may move a fluid 12 (show as saline) into body cavity 4 to engage the particulates 8. And removal lumen 36 may apply a force 14 (shown as a suction force) that moves the fluid 12 and at least some of the particulates 8 out of body cavity 4.

Working device 20 of FIG. 2 also has a sensing lumen 38 with a distal opening 38D on distal face 24. At least one sensor 46 is housed in lumen 38 and operable to detect one or more parameters of fluid 12 and/or cavity 4. For example, sensor 46 may include a pressure sensor, an imaging device, a temperature sensor, a biological sensor, or the like, such that the one or more parameters may include a pressure, an opacity, a temperature, a biological content, or the like. As described further below, each sensor 46 may be configured to communicate the one or more parameters to circulation device 40, either by a wired connection 44 extending proximally through lumen 38 (e.g., FIG. 2), or a wireless connection.

In some aspects, as in FIG. 1, working device 20 is coupled to a circulation device 40 and an energy source 41. Energy source 41 directs energy 10 through working lumen 32. Energy 10 may be applied to hardened mass 6 by any known means. For example, if source 41 is a laser source, the working lumen 32 may deliver laser energy using a forward fire design, wherein the energy is directed along a longitudinal axis of lumen 32; or a lateral (or side fire) design, wherein the energy is directed away from the longitudinal axis. Source 41 need not be a laser source and may, instead, be any source of electric, hydraulic, mechanical, ultrasound, and/or like energy. In some aspects, energy source 41 may be omitted, such as when energy 10 is a mechanical force applied by an elongated tool extended from working lumen 32.

As shown in FIG. 1, circulation device 40 may include a fluid reservoir 50, a delivery module 60, a removal module 70, a filtration element 80, and a controller 90. Each of modules 60 and 70, and controller 90, are shown as being mounted to a housing 42 of circulation device 40, whereas reservoir 50 and filtration element 80 are coupled to device 40. For example, each of circulation device 40, reservoir 50, and filtration element 80 are shown in FIG. 1 as being hung from rack 2, with fluid reservoir 50 being elevated above filtration element 80 housing 42. Any arrangement is possible. Each of these elements is now described.

Fluid reservoir 50 is coupled to delivery module 60 and filtration element 80. For example, in FIG. 1, reservoir 50 is coupled to module 60 by a line 52, and filtration element 80 by a line 54. Fluid reservoir 50 is shown in FIG. 1 as a standard single-use, one-liter bag configured to store fluid 12, although any storage vessel may be used. Lines 52, 54, or any other line described herein, may be formed, in advance or in-situ, using any tubing type, such as any standard, medical grade tubing, including those made of latex, silicone, or the like.

Delivery module 60 is coupled to fluid reservoir 50 and delivery lumen 34. For example, in FIG. 1, module 60 is coupled to reservoir 50 by line 52, and lumen 34 by a line 68. Delivery module 60 may include a pump 64 operable to move fluid 12 from reservoir 50, through module 60, into line 68 and lumen 34 coupled thereto, and out of distal opening 34D into body cavity 4. Removal module 70 is coupled to removal lumen 36 and filtration element 80. For example, in FIG. 1, module 70 is coupled to lumen 36 by a line 78, and filtration element 80 by a line 88. Filtration element 80 is, in turn, coupled to fluid reservoir 50 by line 54, thereby defining a first circulation loop within system 10. Removal module 70 may include a pump 74 operable to move fluid 12 and at least a portion of the particulates 8 from body cavity 4, through distal opening 36D, into removal lumen 36 and line 78 coupled thereto, through module 70, into line 88, through module 80, into line 54, and back into fluid reservoir 50. Accordingly, fluid 12 may be perpetually circulated within the first circulation loop by device 40.

Figure 5:
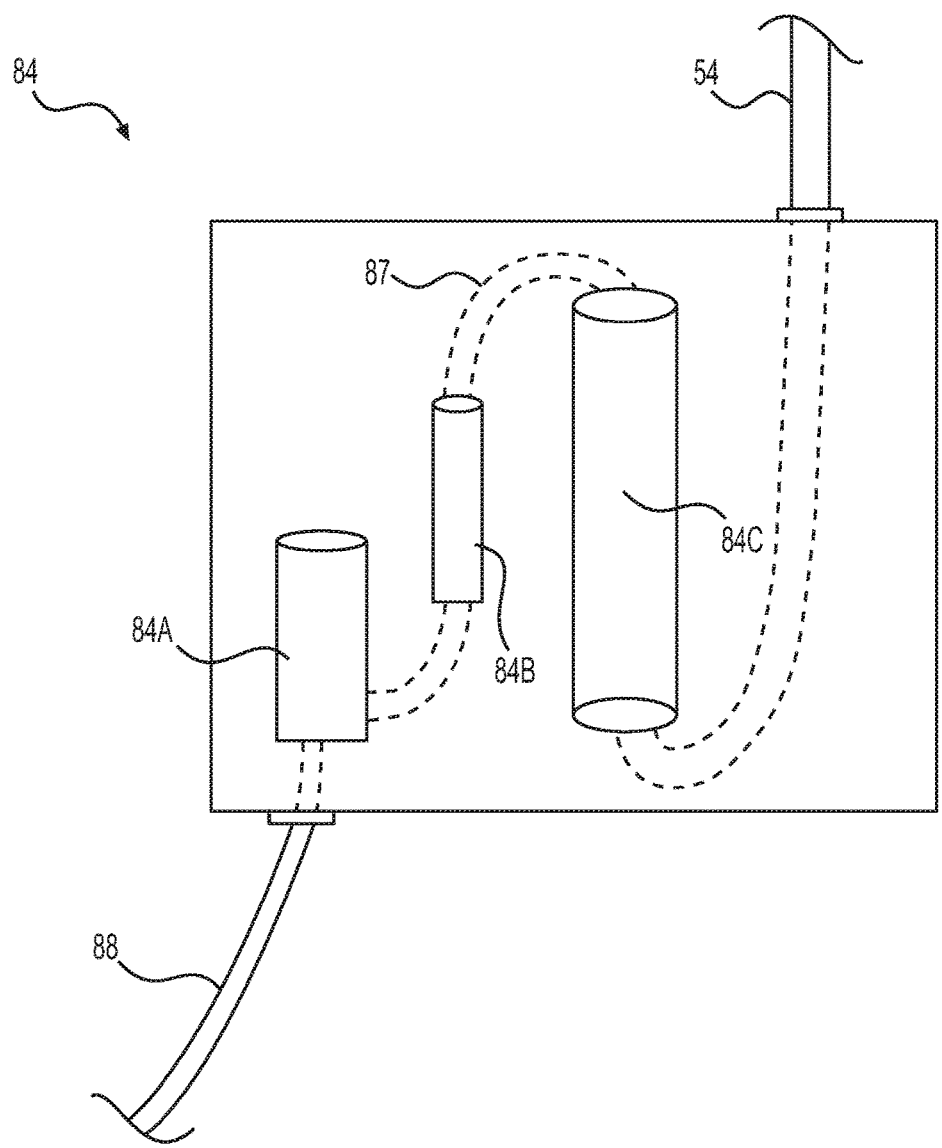
FIG. 5 depicts an exemplary filtering device.

Filtration module 80 is configured to receive fluid 12 from line 88, remove a portion of particulates 8 from fluid 12 using one or more filters 84, and direct the fluid into reservoir 50 through line 54. Aspects of filter 84 are shown in FIGS. 1 and 5. As shown, filter 84 may be a cartridge removable from filtration module 80. This configuration allows filter 84 to be switched out during a procedure to ensure optimal filtration of particulates 8, or substituted to permit removal of a targeted portion of particulates 8. A plurality of filters 84 may be used in series and/or parallel to provide for layered filtration and/or minimize downtime. As shown in FIG. 5, for example, filter 84 may comprise three filtration elements 84A, 84B, and 84C connected by an interior conduit 87 that is placed in communication with lines 54 and 88 when filter 84 is placed in filtration module 80. In some aspects, element 84A may be configured to filter particles 8 of a first size, while element 84B is configured to filter particles 8 of a second or smaller size, and element 84C filters blood, chemicals, or like fluids.

An exemplary controller 90 is illustrated in FIG. 1. As shown, controller 90 includes a processing module 92, an input device 94, and output device 96. Processing module 92 may include any type of processor, including any type of memory, configured to manually or automatically operate system 10. Input device 94 may be a plurality of switches, and output device 96 may be a display screen. For manual operation, processing module 92 may receive a user command from the plurality of switches (e.g., circulate fluid 12 at a desired flow rate, e.g., of approximately 10 ml/s), and operate the delivery and removal modules 60 and 70 based on the user command (e.g., maintain the desired flow rate). In some aspects, controller 90 may guide the user by displaying a parameter detected by at least one sensor 46 on output device 96 (e.g., the flow rate). For automated operation, processing module 92 may receive an initial user command from input device 94 (e.g., maintain a desired pressure of the fluid inside of body cavity 4, e.g., of approximately 6 kPa), receive one or more parameters of the fluid 12 from at least one sensor 46 (e.g., a measurement of said pressure), and operate modules 60 and 70 in response to the one or more parameters (e.g., by adjusting flow rates to maintain the desired pressure).

As shown in FIG. 1, system 10 further comprises a valve 69 coupled to fluid reservoir 50, delivery module 60, and filtration device 80. Valve 69 is operable to form a second circulation loop of system 10. For example, valve 69 may be operated manually to redirect all or a portion of the fluid 12 from line 52, back through delivery module 60, and into filtration device 80 for further processing. Valve 69 may be operated automatically by controller 90. For example, either reservoir 50 or device 80 may include a sensor configured to detect a recirculation parameter of fluid 12 (e.g., blood content), and communicate the recirculation parameter to controller 90. Valve 69 and delivery module 60 may, in turn, be operated with controller 90 to deliver a first portion of fluid 12 to cavity 4 and a second portion of fluid 12 through the second circulation loop, as needed, until the recirculation parameter is no longer detectable by the sensor. Controller 90 may be further configured to operate either or both of delivery and removal modules 60, 70 to maintain a desired pressure within cavity 4. For example, controller 90 may cycle removal module 70 on and off at a predetermined frequency to prevent a pressure imbalance within cavity 4.

An exemplary method 100 for using system 10 is now described with reference to FIGS. 1-4. As shown, method 100 may comprise an initial method step 102 of placing working device 20 into body cavity 4, for example, by placing the distal end 22 of sheath 21 into body cavity 4. As described above, sheath 21 may include a working lumen 32 coupled to energy source 41, a delivery lumen 34 coupled to fluid reservoir 50, and a removal lumen 36 coupled to filtration device 80 and fluid reservoir 50. At least one sensor 46 may be mounted in sensing lumen 38. Each lumen may have a distal opening 32D, 34D, 36D, or 38D that may, for example, be placed adjacent the hardened mass 6 in step 102, as shown in FIGS. 2 and 4.

Another method step 104 may comprise energizing working lumen 32 to generate particulates 8 in body cavity 4. This energizing step may be performed by, for example, producing energy 10 with energy source 41, and directing energy 10 onto hardened mass 6 through working lumen 32, as shown in FIG. 2, wherein energy 10 is depicted as laser energy directed onto a kidney stone. Method 100 may also be used without an energy source 41, wherein step 104 comprises extending an elongated tool from lumen 32 and using a distal end of the elongated tool to generate particles 8.

Figure 4:
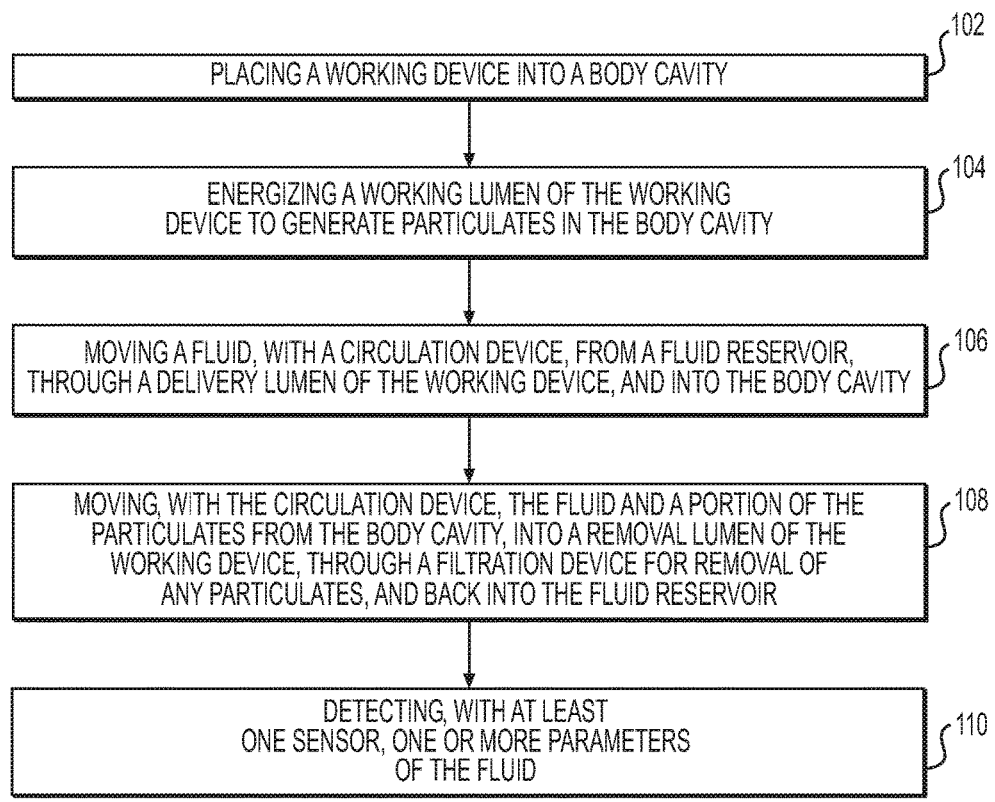
FIG. 4 depicts an exemplary method.

Method 100 of FIG. 4 may be used to move fluid 12 through the first circulation loop. For example, another method step 106 may comprise moving fluid 12, with delivery module 60, from fluid reservoir 50, into delivery lumen 34, and into body cavity 4 through distal opening 34D. This moving step may be performed, for example, by pumping the fluid 12 with pump 64 of delivery module 60. Yet another method step 108 may comprise moving, with removal module 70, the fluid 12 and a portion of the particulates 8 contained therein from body cavity 4, through distal opening 36D, into lumen 36, through filtration device 80 for removal of particulates 8, and back into fluid reservoir 50. This moving step may be performed, for example, by pumping the fluid with pump 74 of removal module 70.

Method steps 106 and 108 may be performed manually. For example, as described above and shown in FIGS. 1-4, controller 90 may be configured to receive a user command from input device 94 (e.g., circulate fluid 12 at a desire flow rate), and operate the delivery and removal modules 60 and 70 based on the user command (e.g., to maintain the flow rate). To guide the user, an additional method step 110 may comprise detecting, with at least one sensor 46, one or more parameters of the fluid 12 in body cavity 4. Additional steps may comprise communicating the one or more parameters to processor 90; and displaying, with processor 90, the one or more parameters on output device 96. Step 110 may further comprise manually adjusting modules 60 or 70 based upon the one or more parameters. For example, as noted above, at least one sensor 46 may include a pressure sensor, such that the one or more parameters include the pressure of fluid 12 inside of cavity 4, and step 110 further comprises manually adjusting the flow rate of modules 60 and 70 based upon pressure displayed on output device 96.

According to other aspects of method 100, delivery and removal modules 60 and 70 may be operated automatically by controller 90 according to an algorithm executed by processor module 92. For example, step 110 may alternatively comprise detecting, with at least one sensor 46, one or more parameters of the fluid 12 in body cavity 4; communicating the one or more parameters to controller 90; and operating the first and second modules 60 and 70 with controller 90 in response to the one or more parameters. For example, at least one sensor 46 may include a pressure sensor, and the one or more parameters of the fluid may include a pressure of fluid 12 in body cavity 4, such that controller 90 may be used to maintain the pressure by operating modules 60 and 70. The algorithm may implement certain safeguards. For example, controller 90 may be used to prevent the pressure of fluid 12 in cavity 4 from exceeding a predetermined maximum, such as the bursting pressure of a kidney, whether modules 60 and 70 are operated manually or automatically.

Method 100 may also be used to move the fluid 12 through the second circulation loop. For example, as described above, a valve 69 may be coupled to fluid reservoir 50, delivery lumen 34, and filtration element 80. Thus, another method step may comprise operating valve 69 to direct the fluid 12 from fluid reservoir 50 and back into filtration element 80 for one or more passes therethrough. If fluid reservoir 50 is made of a translucent material, then valve 69 may be used, for example, to move fluid 12 through the second circulation loop until the fluid 12 in reservoir 50 is visibly different. In some aspects, this alternative method step may comprise detecting, with a sensor, a recirculation parameter of fluid 12 (e.g., blood content); communicating the recirculation parameter to processor 90; and operating, with processor 90, valve 69 and delivery module to circulate the fluid 12 in the second circulation loop, as needed, until the recirculation parameter is no longer detectable by the sensor.

Exemplary aspects of an alternative circulation device 240 are now described with reference to FIG. 3. Any feature of device 240 may be combined with any feature of device 40 system 10, or method 100, with each potential combination being a part of the present disclosure. For ease of reference, like reference numbers have been used to describe devices 40 and 240 wherever possible.

Figure 3A:
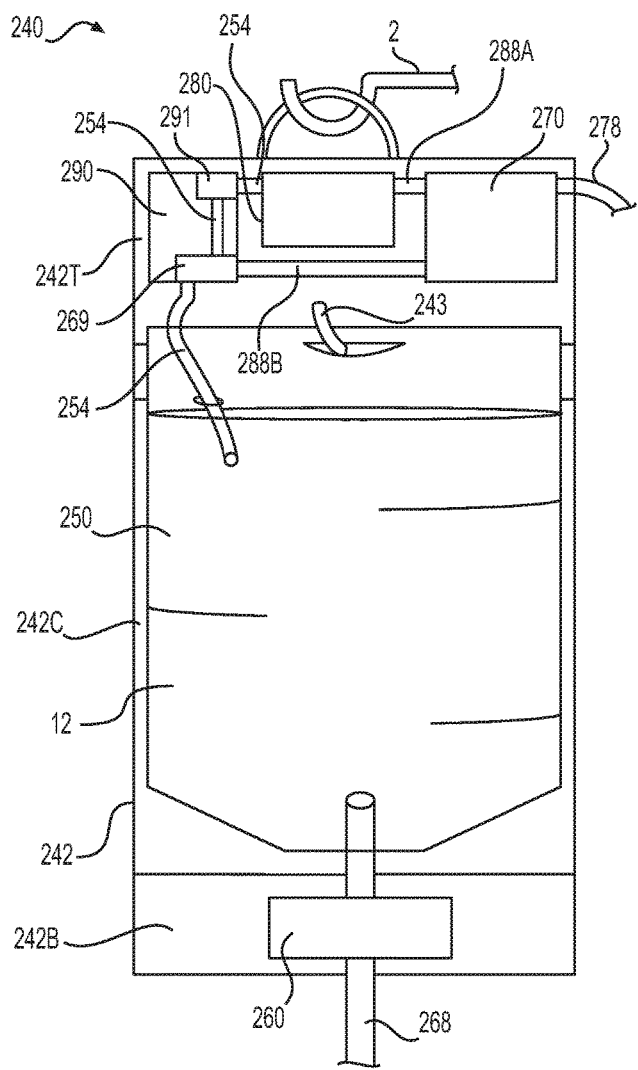
FIG. 3A depicts a front view of another exemplary circulation device.
Figure 3B:
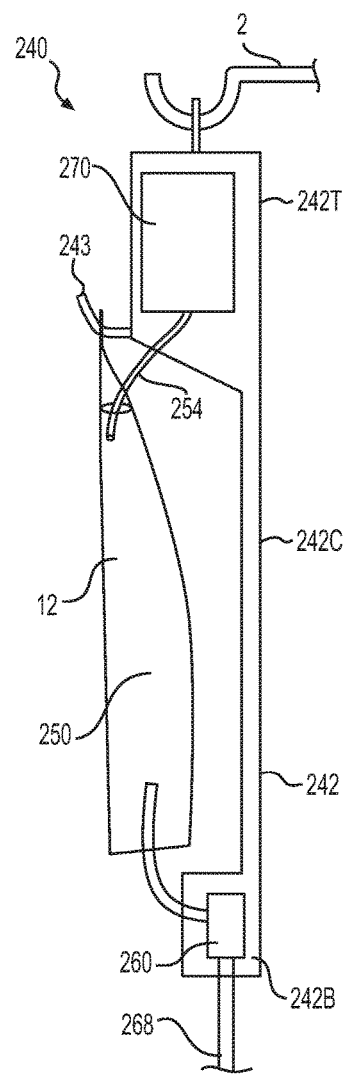
FIG. 3B depicts a side view of the device of FIG. 3A.

Circulation device 240 of FIG. 3, similar to device 40 of FIG. 1, may include a fluid reservoir 250, a delivery module 260, a removal module 270, a filtration element 280, and a controller 290. Device 240 has an elongated housing 242 spanning between a first or top housing portion 242T and a second or bottom housing portion 242B. A third or central portion 242C is defined therebetween to receive fluid reservoir 250, which is depicted in FIG. 3 as being hung from a hanger 243 on housing 242. Delivery module 260 is shown as being mounted within bottom housing portion 242B, whereas removal module 270, filtration element 280, and controller 290 are shown as being mounted within top housing portion 242T. This configuration may allow the entirety of device 240 to be, or example, hung from rack 2 as a single unit.

Module 260 may be configured to move fluid 12 from reservoir 250 into delivery lumen 34 through a line 268, as shown in FIG. 3. As also shown, module 270 may be configured to move fluid 12 and a portion of the particulates 8 from body cavity 4, into removal lumen 36 through a line 278, through module 270, into filtration device 280 through a line 288A, and back into fluid reservoir 250 through line 254, thereby defining the first circulation loop, one including body cavity 4.

A second circulation loop is also defined by device 240. The second circulation loop does not include body cavity 4. For example, in FIG. 4, controller 290 includes a valve 269 and a sensor 291. Valve 269 is coupled to fluid reservoir 250 and filtration device 280 by a line 254, and module 270 by a line 288B, thereby defining the second circulation loop, wherein fluid 12 may be recirculated back through device 280. Sensor 291 is positioned on, for example, line 254 to measure a recirculation parameter of the fluid 12 exiting from filtration module 280 (e.g., blood content). If fluid 12 does not meet a set of criteria established by controller 290, then valve 269 may be operated to recirculate all or a portion of fluid 12 through the second circulation loop (e.g., through line 288B), as needed before returning to reservoir 50 or body cavity 4, for example, until the recirculation parameter is no longer detectable. As shown, the proximity of removal module 270 and filtration device 280 permits the second circulation loop to be shorter.

Any step of method 100 may be modified to accommodate the structure of circulation device 240. For example, because the second circulation loop is comparatively shorter with device 240, step 112 may be modified to circulate the fluid 12 between the first and second circulation loops at a predetermined ratio. For example, the fluid 12 may be moved through filtration device 280 a plurality of times before passing into fluid reservoir 250, which may be large enough to permit these additional filtration loops without disrupting the performance of system 10.

Still other alternative aspects of system 10 are now described. As before, any feature of these alternative aspects may be combined to create variations of system 10, each potential variation being part of this disclosure. For example, working device 20 has been described as having a certain number of lumens (e.g., four), each lumen being configured to perform a different function. Working device 20 may have any number of lumens, each configured to perform any number of functions. Device 20 may include additional filtration elements. For example, distal opening 36D of removal lumen 36 (FIG. 2) may have filter or screen placed therein to, for example, prevent any particulates 8 of a predetermined size from entering and potentially plugging lumen 36.

Working device 20 has been described as including a sensor lumen 38 with at least one sensor 46. Either of these elements may be modified. For example, in lieu of sensory lumen 38, working device 20 may have a sensor bay extending proximally into distal face 22 to receive a sensor module. As with sensor 46, any number of sensors may be included in the sensor module, which may communicate wired or wirelessly with controller 90 to perform any function described herein. Additional sensors may be deployed through system 10. For example, additional sensors, like sensor 291, may be deployed in fluid reservoir 50, delivery module 60, removal module 70, or filtration device 80, each sensor being operable to detect one or more parameters of fluid 12 at any point within the first or second circulation loops defined above.

Circulation devices 40 and 240 have been described as including a delivery module 60 or 260, and a removal module 70 or 270. Either of these modules may be removable from or integral with system 10. For example, modules 60 and 70 of device 40 may be removably coupled to housing 42 for ease of replacement. Alternatively, certain functions of modules 60 and 70 may be performed by a secondary device coupled with working device 20. For example, either or both modules 50 and 60 may be coupled to a port of housing 42 that, in turn, is coupled with an external fluid pump associated with the secondary device. Modules 50 and 60 may also be replaceable and/or expandable to provide system 10 with additional capabilities. For example, each module 60 and 70 may be further configured to modify the temperature of fluid 12; introduce another agent to fluid 12, such as a contrasting agent, a diluting agent, or a medicating agent; or otherwise modify fluid 12 for use during a particular procedure. These capabilities may be realized by swapping out one module for another, by adding an expansion device to either module, or by otherwise placing these modules in communication with another device or fluid source.

Filtration device 80, for example, has been described as being coupled to fluid reservoir 50 and removal module 70, although this is not required as one or more filtration devices 80 may be located anywhere throughout system 10. Any type of filtration technology may also be used, including those deploying ultraviolet light, or other low friction filtration medium configured to minimize the force required to move fluid 12 through device 80. Consistent with above, these capabilities may either be integral with filtration device 80, included with filter 84, or provided by another modular element. For example, filter 84 may incorporate any number of integral or removable filtration elements, sensors and/or valves. In some aspects, filter 84 may be configured to define one or more additional or third circulation loops within system 10. A third circulation loop may, for example, be formed into filter 84 by adding a return portion to interior conduit 87 and a valve similar to valve 69 described herein (e.g., FIG. 1).

Each of fluid reservoirs 50 and 250 have been described, for example, as a single-use 1 liter bag, such as those commonly used for saline, thereby allowing system 10 to be used with existing supplies. This is not required. For example, fluid reservoir 250 may be an integral component of circulation device 240, such as a compartment of housing 242. Although described as a single reservoir, it should be appreciated that the storage features of reservoir 250 may also be distributed throughout system 10. For example, module 260, module 270, and device 280 may each include their own fluid reservoir(s) to ensure smooth operation of system 10, even if reservoir 250 is temporarily disconnected. In some aspects, reservoir 250 may be omitted if the distributed capacity of these elements is equal or greater in capacity to reservoir 50.

As before any step of method 100 shown in FIG. 4 may be modified to accommodate the structure of any of these alternate aspects.

Numerous attributes of system 10 and method 100 are apparent from the above disclosure. For example, some aspects of system 10 method may help to reduce the operating times and associated costs of lithotripsy procedures by allowing the surgeon to work continuously with clear visualization. By recirculating fluid 12, as opposed to continually replacing reservoir 50, system 10 and method 100 may also reduce waste. Other aspects may also enhance safety, as noted above, by safeguarding against the over pressurization of cavity 4 and providing additional means for analyzing various parameters of fluid 12 as it circulated through system 10. For example, any of the sensors described above may be used to alert the surgeon if the fluid 12 being removed from cavity 4 contains an unacceptable amount of particulates, blood, or the like.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A system comprising:
a tubular member with a plurality of lumens extending longitudinally therethrough including a working lumen, a delivery lumen, and a removal lumen;
a filtration device, wherein the filtration device includes at least three filters connected by a fluid conduit;
at least one sensor operable to detect one or more parameters of a fluid;
a delivery module coupled to a fluid reservoir and the delivery lumen;
a removal module coupled to the removal lumen and the filtration device;
a controller; and
a valve coupled to the fluid reservoir, the delivery module, and the filtration device,
wherein the fluid reservoir is coupled to the filtration device so as to define at least one circulation loop to circulate a fluid when the tubular member is placed in a body cavity, and wherein the valve is operable with the controller to direct the fluid from the fluid reservoir back into the filtration device in response to the one or more parameters to form a second circulation loop.

2. The system of claim 1, wherein the at least one sensor is located on a distal end of the tubular member.

3. The system of claim 2, wherein the at least one sensor includes a pressure sensor and the one or more parameters include a pressure of the fluid in the body cavity.

4. The system of claim 2, wherein the at least one sensor includes a blood detector and the one or more parameters include an amount of blood in the fluid.

5. The system of claim 1, further comprising a laser source coupled to the working lumen.

6. The system of claim 1, wherein the fluid is saline and the fluid reservoir is a saline bag.

7. The system of claim 1, wherein the at least three filters are connected in series by the fluid conduit.

8. A system comprising:
a sheath including a working lumen, a delivery lumen, and a removal lumen;

at least one sensor operable to detect one or more parameters of a fluid;
a filtration device, wherein the filtration device includes one or more filters in a removable filter cartridge;
a circulation device including a first pump coupled to a fluid reservoir and the delivery lumen, a second pump coupled to the removal lumen and the filtration device, and a controller that operates the first and second pumps in response to the one or more parameters; and
a valve,
wherein the fluid reservoir is coupled to the filtration device so as to define at least one circulation loop to circulate a fluid when the sheath is placed in a body cavity, and wherein the valve controls a portion of the at least one circulation loop and is operable with the controller to direct the fluid from the fluid reservoir and back into the filtration device in response to the one or more parameters to form a second circulation loop.

9. The system of claim 8, wherein the at least one sensor includes one of a pressure sensor, an imaging device, and a temperature sensor.

10. The system of claim 8, wherein the at least one sensor is located on the sheath and includes a pressure sensor, the one or more parameters include a predetermined fluid pressure in the body cavity, and the controller maintains the predetermined fluid pressure by operation of the first and second pumps.

11. The system of claim 8, wherein the filtration device includes three or more filters connected in series by a fluid conduit, wherein the three or more filters are removably attached to the filtration device via the removable filter cartridge.

12. The system of claim 8, wherein at least the first and second pumps are removably mounted to a housing of the circulation device.

13. The system of claim 12, wherein the controller further comprises an input device and an output device on the housing of the circulation device, and wherein the first and second pumps are separately adjustable to control a pressure within the body cavity.

14. A system comprising:
a tubular member including a working lumen, a delivery lumen, and a removal lumen;
at least one sensor operable to detect one or more parameters of a fluid;
a filtration device;
a circulation device including a first pump coupled to a fluid reservoir and the delivery lumen, a second pump coupled to the removal lumen and the filtration device, wherein the fluid reservoir is coupled to the filtration device so as to define a first circulation loop when the tubular member is placed in a body cavity;
a controller that operates the first and second pumps in response to the one or more parameters; and
a valve coupled to the fluid reservoir, the first pump, and the filtration device, wherein the valve is operable to form a second circulation loop to direct at least a portion of fluid from the fluid reservoir to the filtration device.

15. The system of claim 14, wherein the filtration device includes a removable filter cartridge including at least three filters connected in series by a fluid conduit.

16. The system of claim 14, wherein the at least one sensor is positioned in either the reservoir or the filtration device, and wherein if the at least one sensor detects blood in the fluid, the controller is configured to signal the valve to direct the portion of the fluid through the second circulation loop.

17. The system of claim 14, wherein the at least one sensor is located on the tubular member and includes a pressure sensor, the one or more parameters include a predetermined fluid pressure in the body cavity, and the controller maintains the predetermined fluid pressure by operation of the first and second pumps.

* * * * *